US006211160B1

(12) United States Patent
Wilson et al.

(10) Patent No.: US 6,211,160 B1
(45) Date of Patent: Apr. 3, 2001

(54) METHOD FOR TOLERIZING A MAMMALIAN PATIENT TO ADMINISTRATION OF GENE THERAPY VIRUS VECTORS

(75) Inventors: James M. Wilson, Gladwyne; Youhai Chen, Broomall, both of PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 08/889,930

(22) Filed: Jul. 10, 1997

Related U.S. Application Data

(60) Provisional application No. 60/025,549, filed on Sep. 6, 1996.

(51) Int. Cl.$^7$ ........................... A61K 48/00; C12N 15/63; C12N 15/79

(52) U.S. Cl. ..................... 514/44; 424/93.21; 424/199.1; 424/93.6; 424/204.1; 424/205.1; 424/233.1; 435/320.1; 435/375

(58) Field of Search ............................. 424/199.1, 204.1, 424/205.1, 93.1, 93.2, 93.21, 93.6, 233.1; 514/44; 435/320.1, 375

(56) References Cited

FOREIGN PATENT DOCUMENTS

| | | |
|---|---|---|
| WO91/12816 | 9/1991 | (WO). |
| WO95/27500 | 10/1995 | (WO). |
| WO 96/12406 | 5/1996 | (WO). |
| WO96/14874 | 5/1996 | (WO). |
| WO 96/26285 | 8/1996 | (WO). |
| WO96/39176 | 12/1996 | (WO). |

OTHER PUBLICATIONS

Madeley (1968) J. Hyg., vol. 66, 89–107.*
Chung et al. (1987) Vaccine, vol. 5, 175–178.*
McCray et al. (1995) J. Clin. Invest., vol. 95, 2620–2632.*
Yei et al. (1994) Gene Therapy, vol. 1, 192–200.*
Yang et al. (Apr. 1995) Journal of Virology, vol. 69 (4), 2004–2015.*
Putnack et al. (1991) Am. J. Trop. Med. Hyg., vol. 45 (2), 159–167.*
Y. Chen et al, "Peripheral Deletion of Antigen–Reactive T Cells in Oral Tolerance", *Nature*, 376:177–180 (Jul. 13, 1995).
Y. Chen et al, "Oral Tolerance in Myelin Basic Protein T–Cell Receptor Transgenic Mice: Suppression of Autoimmune Encephalomyelitis and Dose–Dependent Induction of Regulatory Cells", *Proc. Natl. Acad. Sci. USA*, 93:388–391 (Jan., 1996).
Y. Chen et al, "Regulatory T Cell Clones Induced by Oral Tolerance Suppression of Autoimmune Encephalomyelitis", *Science*, 265:1237–1240 (Aug. 26, 1994).

Y. Ilan et al, "Oral Tolerization to Adenoviral Proteins Permits Repeated Adenovirus–Mediated Gene Therapy in Rats with Pre–Existing Immunity to Adednoviruses", *Hepatology*, 27(5):1368–1376 (May, 1998).
Y. Ilan et al, "Oral Tolerization to Adenoviral Antigens Permits Long–Term Gene Expression Using Recombinant Adenoviral Vectors", *J. Clin. Invest.*, 99(5):1098–1106 (Mar., 1997).
H. Kagami et al, "Repetitive Adenovirus Administration to the Parotid Gland: Role of Immunological Barriers and Induction of Oral Tolerance", *Human Gene Therapy*, 9(3):305–313 (Feb. 10, 1998).
M. Takahashi et al, "Long Term Correction of Bilirubin–UDP–glucuronosyltransferase Deficiency in Gunn Rats by Administration of a Recombinant Adenovirus During the Neonatal Period", *J. Biol. Chem.*, 271(43):26536–26542 (Oct. 25, 1996).
A. Kass–Eisler et al, "Circumventing the Immune Response to Adenovirus–Mediated Gene Therapy", *Gene Ther.*, 3(2):154–162 (Feb., 1996) (Abstract only).
J. Walter et al, "Successful Expression of Human Factor IX Following Repeat Administration of Adenoviral Vector in Mice", *Proc. Natl. Acad. Sci. USA*, 93(7):3056–3061 (Apr. 2, 1996).
Y. Chen et al. "Inductive Event sin Oral Tolerance in the TCR Transgenic Adoptive Transfer Model", *Cellular Immunology*, 178:62–68 (1997).
S. Yei et al., "Adenovirus–Mediated Gene Transfer for Cystic Fibrosis: Quantitative Evaluation of Repeated in Vivo Vector Administration to the Lung", *Gene Therapy*, 1:192–200 (1994).
Z. Zsengeller et al., "Persistence of Replication–Deficient Adenovirus–Mediated Gene Transfer in Lungs to Immune–Deficient (nu/nu) Mice", *Human Gene Therapy*, 6:457–467 (Apr. 1995).
J. Zabner et al., "Adenovirus–Mediated Gene Transfer Transiently Corrects the Chloride Transport Defect in Nasal Epithelia of Patients with Cystic Fibrosis", *Cell*, 75:207–216 (Oct. 22, 1993).
R. Crystal et al., "Administration of an Adenovirus Containing the Human CFTR cDNA to the Respiratory Tract of Individuals with Cystic Fibrosis", *Nature Genetics*, 8:42–51 (Sep. 1994).

(List continued on next page.)

*Primary Examiner*—Karen M. Hauda
(74) *Attorney, Agent, or Firm*—Howson and Howson (57) ABSTRACT

A method for tolerizing a mammalian subject to administration of a live virus carrying a gene for delivery to a cell of the subject is disclosed. The method entails administering to the subject a suitable amount of an inactivated virus prior to administration of the live virus. The prior administration of the inactivated virus suppresses anti–virus cytotoxic T cells, permitting longer transgene persistence once the live virus is administered, and permitting effective readministration of live virus.

11 Claims, 3 Drawing Sheets

OTHER PUBLICATIONS

R. Vemuru et al, "Immune Tolerance to a Defined Heterologous Antigen After Intrasplenic Hepatocyte Transplantation: Implications for Gene Therapy", *FASEB J.*, 6:2836–2842 (Jul., 1992).

Y. Yang et al., "Cellular and Humoral Immune Responses to Viral Antigens Create Barriers to Lung–Directed Gene Therapy with Recombinant Adenovirus", *J. of Virology*, 69(4):2004–2015 (Apr. 1995).

T. Smith et al., "Adenovirus Mediated Expression of Therapeutic Plasma Levels of Human Factor IX in Mice", *Gene Therapy*, 5:397–401 (Dec. 1993).

K. Kozarsky et al., "In Vivo Correction of Low Density Lipoprotein Receptor Deficiency in the Watanabe Heritable Hyperlipidemic Rabbit with Recombinant Adenoviruses", *J. of Biological Chemistry*, 269(18):13695–13702 (May 1994).

Y. Yang et al., "Transient Subversion of CD40 Ligand Function Diminishes Immune Responses to Adenovirus Vectors in Mouse Liver and Lung Tissues", *J. of Virology*, 70(9)6370–6376(Sep. 1996).

* cited by examiner

METHOD FOR TOLERIZING A MAMMALIAN PATIENT TO ADMINISTRATION OF GENE THERAPY VIRUS VECTORS

CROSS-REFERENCE TO RELATED APPLICATIONS

This application claims priority of U.S. Provisional Patent Application Ser. No. 60/025,549, filed Sep. 6, 1996.

This invention was supported by the National Institute of Health Grant No. DK47757. The United States government has rights in this invention.

FIELD OF THE INVENTION

The present invention relates to the field of somatic gene therapy and methods useful therein.

BACKGROUND OF THE INVENTION

Immune responses of the recipient to the viral vectors used in somatic gene therapy, i.e., to the viral proteins of the vector, and/or to the transgene carried by the vector, and/or the virus-infected cells, have emerged as recurring problems in the initial application of gene therapy technology to animals and humans [Yang et al, *J. Virol.*, 69:2004–2015 (1995) (Yang I)]. In virtually all models, including lung-directed and liver-directed gene therapy, expression of the transgene is transient and associated with the development of pathology at the site of gene transfer.

The transient nature of transgene expression from recombinant adenoviruses, for example, has been found to be due, in part, to the development of antigen specific cellular immune responses to the virus-infected cells and their subsequent elimination by the host. The collaboration of CTLs directed against newly synthesized viral proteins and viral specific T helper cells [Zabner et al, *Cell*, 75:207–216 (1993); Crystal et al, *Nat. Genet.*, 8:42–51 (1994)] leads to the destruction of the virus-infected cells. These immune responses have also been noted to cause the occurrence of associated hepatitis that develops in recipients of in vivo liver-directed gene therapy within 2–3 weeks of initial treatment, and myositis in recipients of in vivo muscle-directed gene therapy.

Another antigenic target for immune mediated clearance of virus-infected cells is the product of the transgene. CTLs are an important effector in the destruction of target cells with activation occurring in some cases in the context of the transgene product, as well as the viral-synthesized proteins, both presented by MHC class I molecules [Yang I; and Zsengeller et al, *Hum. Gene Thera.*, 6:457–467 (1995)].

Another limitation of the use of recombinant virus vectors for gene therapy has been the difficulty in obtaining detectable gene transfer upon a second administration of virus. This limitation is particularly problematic in the treatment of single gene inherited disorders or chronic diseases, such as cystic fibrosis (CF), that will require repeated therapies to obtain life-long genetic reconstitution. Diminished gene transfer following a second therapy has been demonstrated in a wide variety of animal models following intravenous or intratracheal delivery of adenovirus vectors [T. Smith et al, *Gene Thera.*, 5:397 (1993); S. Yei et al, *Gene Thera.*, 1:192–200 (1994); K. Kozarsky et al, *J. Biol. Chem.*, 269:13695 (1994)]. Similar difficulties have been noted when the viral vector is other than adenovirus, i.e., retrovirus, vaccinia, and the like. In each case, resistance to repeated gene therapy was associated with the development of neutralizing anti-virus antibodies, which thwarted successful gene transfer following a second administration of virus.

Proposed solutions to these anti-viral immune responses have to date involved new designs of the virus vectors which employ fewer viral genes, as well as the pre- or co-administration of immune modulators, such as anti-CD40 ligands and other modulators identified in the art [See, e.g., Yang et al., *J. Virol.*, 70(9) (September, 1996); International Patent Application No. WO96/12406, published May 2, 1996; and International Patent Application No. PCT/US96/03035, all incorporated herein by reference].

Nevertheless, the successful induction of specific immune tolerance to the new gene products (both virus products and transgene products) of the recombinant gene therapy vectors remains one of the most formidable challenges in gene therapy. Failure to establish immune tolerance to viral gene therapy vectors may lead to immune rejection of the transgene-expressing cells and therefore loss of transgenes.

There exists a need in the art for methods and compositions which enable the induction of specific immunologic tolerance to viral vector capsid proteins and both viral gene and transgene products being introduced and expressed in mammalian cells by general gene therapy methods.

SUMMARY OF THE INVENTION

The present invention provides a solution to the aforementioned need in the art by providing a method for eliminating the immune barrier impeding long-term gene therapy by selectively tolerizing a mammalian subject to multiple administrations of a live recombinant virus carrying a gene for delivery to a cell of said subject. This method involves administering to the subject a suitable amount of an inactivated virus prior to administration of a first live recombinant virus. The inactivated virus may be a whole virus, a replication defective virus, a previously inactivated copy of the live recombinant virus carrying a transgene, or a previously inactivated recombinant virus without a transgene. Inactivated virus is preferably administered via an oral or intravenous route. The administration of the inactivated virus essentially deactivates T cells specific for viral antigens, before the live recombinant virus carrying the transgene is administered.

Other aspects and advantages of the present invention are described further in the following detailed description of the preferred embodiments thereof.

DETAILED DESCRIPTION OF THE INVENTION

The method of the present invention provides for selectively tolerizing a mammalian subject to multiple administrations of a recombinant gene therapy virus which carries a therapeutic gene (transgene) for delivery to a cell, wherein the transgene product is expressed in vivo. According to the present invention, it has been observed unexpectedly that administering to a prospective candidate for gene therapy treatment a suitably high dosage of an inactivated virus prior to administration of a live recombinant virus carrying a transgene suppresses the anti-virus immune responses mounted by the patient and permits prolonged transgene expression in vivo.

As detailed in Example 1 below, oral administration of a heat-inactivated, UV-irradiated rAd5-LacZ induced immune suppression of anti-adenoviral antigen immunity in mice that were subsequently challenged with live rAd5-LacZ. Immune tolerance was measured by determining the persistence of the transgene, LacZ, in the mouse tissue at various days following challenge. Mice receiving the live rAd-LacZ did not reject the live recombinant virus carrying the transgene. In contrast, mice which received similar oral doses of live rAd5-LacZ or live rAd5-LacZ-infected splenocytes, displayed strong anti-adenoviral antigen immunity upon presentation with the live virus. This result indicated that prior administration of the inactivated or killed virus induced immune tolerance in the mice for the administration of the live recombinant virus carrying the transgene.

Additional experiments described in detail in Example 2 below were conducted to determine if the immune tolerance to subsequent administration of the live recombinant virus resulting from oral administration of the inactivated virus could be similarly induced by iv administration of the inactivated virus. Following the same protocol as in Example 1, mice were administered phosphate buffered saline as a control or inactivated rAd5-LacZ orally or the same dosage of inactivated rAd5-LacZ i.v. Subsequently, all three groups of mice were challenged with live rAd-LacZ.

Figure 1A:
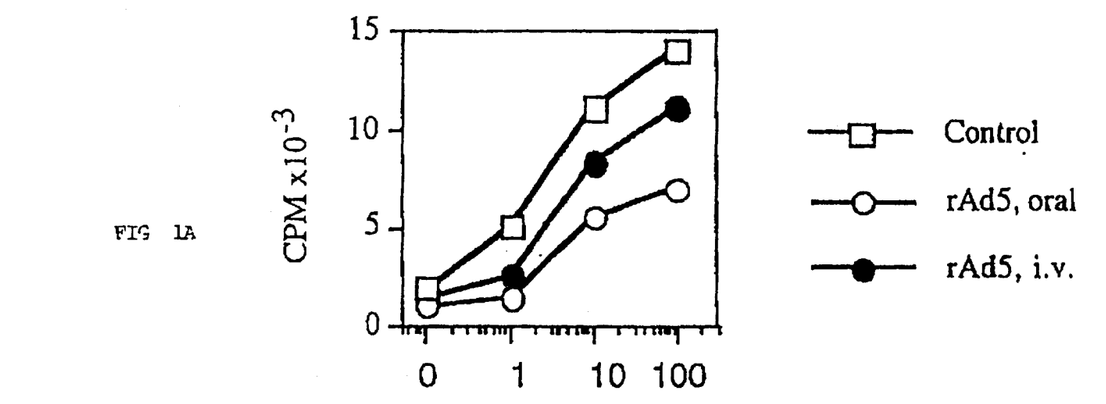
FIG. 1A is a graphical plot of the data obtained from the proliferation assay described in Example 2. The graph plots viral proliferation in mouse splenocytes, measured by radioactivity of tritiated thymidine in units of $CPM \times 10^{-3}$ as a function of the number of recombinant adenovirus serotype 5 virus carrying a beta-galactosidase gene $(rAd5-LacZ)/ml \times 10^{-8}$. C57BL/6 mice were fed with (1) PBS (open square), (2) $10^{12}$ heat-inactivated, UV-irradiated rAd5-LacZ ("dead" rAd5-LacZ) (open circle), or cells from mice injected intravenously (iv) with $10^{12}$ dead rAd5-LacZ (filled circle), and subsequently challenged with live rAD5-LacZ. Splenocytes were harvested for analysis 10 days after administration of live rAd5-LacZ.

Mice splenocytes were subjected to a proliferation assay to measure immune tolerance based on a comparison of the number of splenocytes which proliferated as a function of the number of live rAd5-LacZ/ml. As illustrated in FIG. 1A, splenocytes decreased in number for the mice administered the inactivated virus, both orally and intravenously in comparison to the control.

Figure 1B:
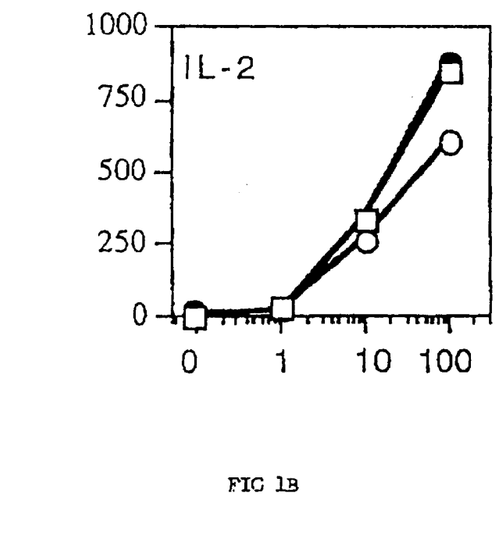
FIG. 1B is a graphical plot of the data obtained from the cytokine (IL-2) assay described in Example 2. The graph plots IL-2 in pg/ml as a function of number of rAd5-LacZ/$ml \times 10^{-8}$ for the same mice as reported in FIG. 1A.
Figure 1C:
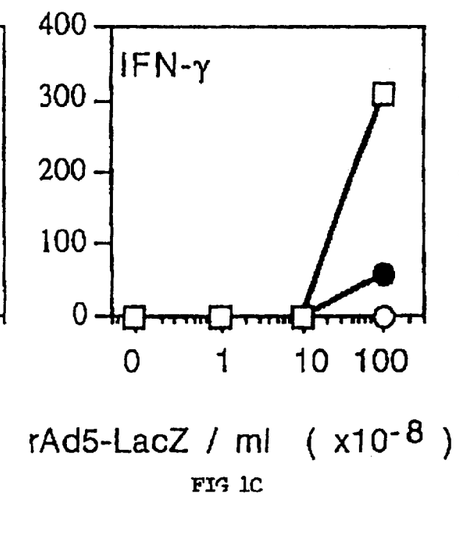
FIG. 1C is a graphical plot of the data obtained from the cytokine (IFN-γ) assay described in Example 2. The graph plots IFN-γ in pg/ml as a function of number of rAd5-LacZ/ml×10$^{-8}$ for the same mice as reported in FIG. 1A.
Figure 1D:
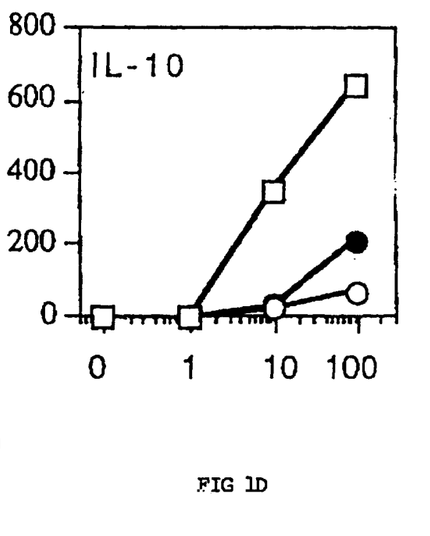
FIG. 1D is a graphical plot of the data obtained from the cytokine (IL-10) assay described in Example 2. The graph plots IL-10 in pg/ml as a function of number of rAd5-LacZ/ml×10$^{-8}$ for the same mice as reported in FIG. 1A.

Cytokine assays were conducted on the same mice to assess the mechanism of the tolerance. As shown in FIG. 1B IL-12 production was suppressed only with the orally administered inactivated virus. However, both IFN-γ (FIG. 1C) and IL-10 (FIG. 1D) were suppressed in response to administration of orally or i.v. administered inactivated virus in comparison to the control. Oral administration suppressed the two latter cytokines to a greater extent than both the control and the iv administered inactivated virus.

Figure 2:
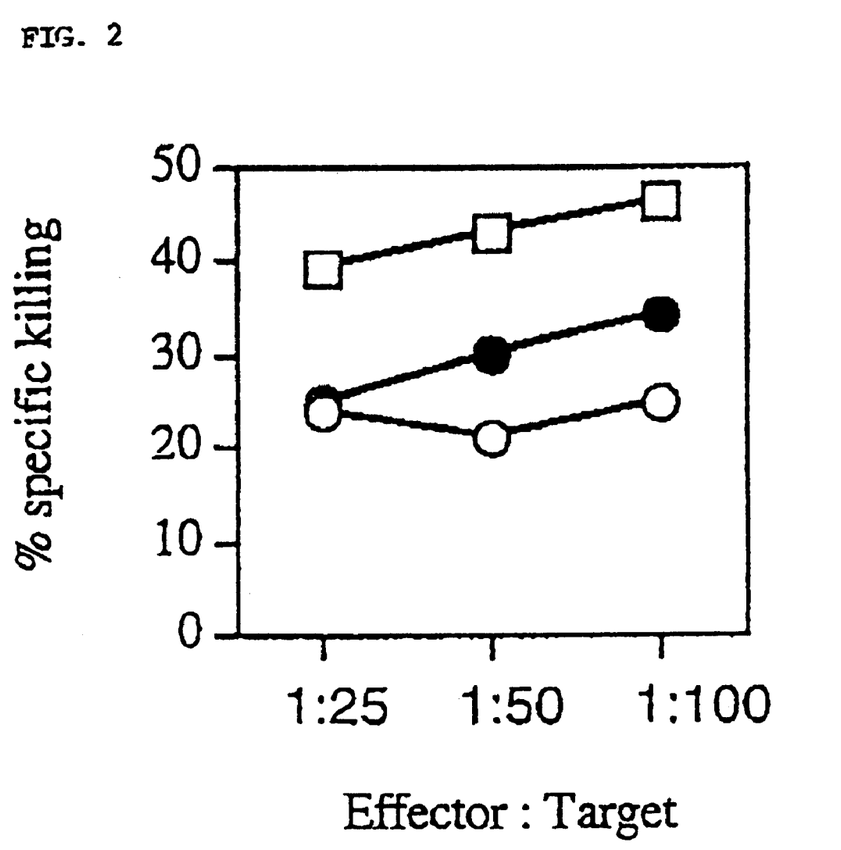
FIG. 2 is a graphical plot of the data obtained from the cytotoxicity assay described in Example 3. The symbols report mice treated as described in Example 1. Open square, fed with PBS; open circle, fed with 10$^{12}$ dead rAd5-LacZ; filled circle, injected intravenously with 10$^{12}$ dead rAd5-LacZ. The graph plots % specific killing of splenocytes as a function of effector-to-target ratio.
Figure 3A:
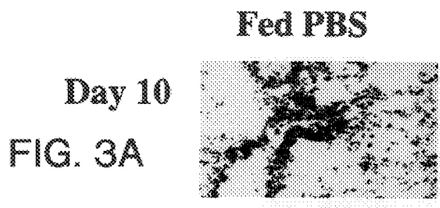
FIG. 3A is a histogram of mouse lung tissue for mice fed with PBS and subsequently challenged with live rAd5-LacZ at day 10 following challenge. LacZ gene expression is observed.
Figure 3B:
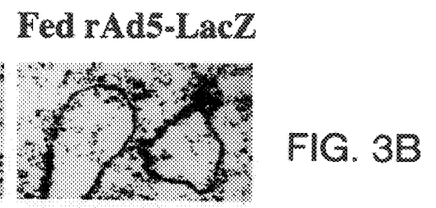
FIG. 3B is a histogram of mouse lung tissue for mice fed with dead rAd5-LacZ and subsequently challenged with live rAd5-LacZ at day 10 following challenge. LacZ gene expression is observed.
Figure 3C:
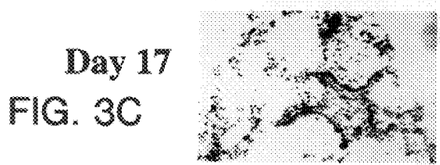
FIG. 3C is a histogram of mouse lung tissue for mice fed with PBS and subsequently challenged with live rAd5-LacZ at day 17 following challenge. LacZ gene expression is observed.
Figure 3D:
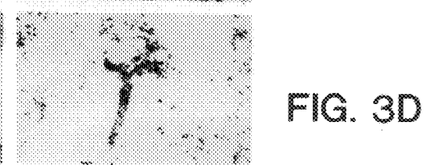
FIG. 3D is a histogram of mouse lung tissue for mice fed with dead rAd5-LacZ and subsequently challenged with live rAd5-LacZ at day 17 following challenge. LacZ gene expression is observed.
Figure 3E:
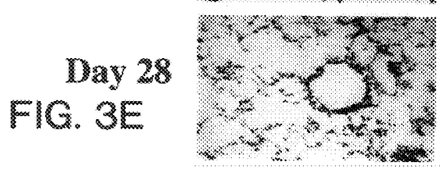
FIG. 3E is a histogram of mouse lung tissue for mice fed with PBS and subsequently challenged with live rAd5-LacZ at day 28 following challenge. No LacZ gene expression is observed.
Figure 3F:
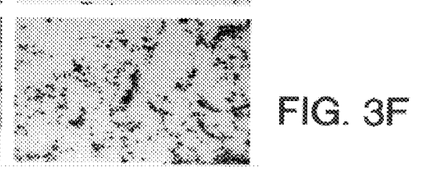
FIG. 3F is a histogram of mouse lung tissue for mice fed with dead rAd5-LacZ and subsequently challenged with live rAd5-LacZ at day 28 following challenge. LacZ gene expression is observed.

Because immune rejection of transgene-expressing cells are mediated primarily by cytotoxic T cells, anti-adenovirus cytotoxicity to oral or intravenous administration of dead viral antigens was tested by $^3$H-thymidine release assay (JAM assay) as described in Example 3. As shown in FIG. 2, both oral and intravenous administrations of dead rAd5-LacZ suppressed generation of adenovirus-specific cytotoxic T cells, although under these conditions, the oral route appeared to be more effective than the intravenous route. It is to be noted that this is the first demonstration that oral administration of antigens activates anti-virus cytotoxic T cells.

Resistance to re-administration of recombinant virus may be partially mediated by neutralizing antibodies specific for viral antigens. Therefor to determine whether oral administration of rAd5-LacZ suppresses humoral immunity, anti-adenovirus antibody responses in mice fed rAd5-LacZ were examined by conventional methods as described in Example 4 below. A 40–60% suppression was observed for anti-adenovirus IgM and IgG responses. These data strongly suggest that specific immunologic tolerance can be induced by oral or intravenous administration of inactivated virus, but that oral route may be more effective than intravenous route.

To test whether oral tolerance helps to prolong the in vivo transgene expression, LacZ gene expression was examined by X-gal histochemistry according to standard procedures as described in Example 5 for mice administered inactivated rAd5-LacZ or PBS orally and subsequently challenged with live recombinant virus as in Example 2. As indicated in the FIGS. 3A through 3F, LacZ gene expression lasted approximately 17 days in lung tissue of non-tolerized (PBS-fed) mice. The expression of the transgene was prolonged to at least 28 days in mice fed 10$^{12}$ dead rAd5-LacZ prior to live virus challenge, according to this invention.

Thus, pre-administration of inactivated virus has a 'tolerizing' effect upon subsequent administration of the live recombinant virus. This allows prolonged persistence of transgene expression from a single administration of recombinant virus and allows effective multiple administrations of a recombinant virus carrying the transgene to the gene therapy candidate, i.e., a patient suffering from a disorder due to the mutation, deletion or functional deletion of a normal gene or a patient with an acquired disease.

The method of the present invention is useful for any recombinant virus carrying a transgene useful in gene therapy, such as adenovirus, adeno-associated virus, retrovirus and others. Many suitable recombinant viruses vectors carrying a host of desired genes are presently known to the art. The design of the recombinant gene therapy virus is not a limitation on this method, nor is the selection of the transgene and the regulatory sequences required to express the transgene product in vivo. The selection of the virus is well within the skill of the art of gene therapy.

Similarly, it is anticipated that the method of this invention will operate to suppress unwanted anti-virus and possibly, anti-transgene, immune responses regardless of the disease or disorder being treated. Thus, this method is expected to have broad applicability in the field of gene therapy.

In one embodiment of this invention, the inactivated virus and the live recombinant virus carrying the transgene have substantially, and preferably completely, identical viral capsid proteins and viral genes. For example, as described in the examples below, the "dead virus" is simply the same recombinant virus, except that it has been killed or inactivated. The subsequent live virus administration uses the same virus, which has not been inactivated.

Alternatively, the inactivated virus may be the same virus, but does not carry a transgene, i.e., an "empty" recombinant virus.

In still another embodiment, the inactivated virus and live virus may have antigenically related viral proteins. "Antigenically related" means that each virus activates an immune response capable of eliminating the other virus, because each virus expresses a gene product with at least one antigen present on the other gene product.

In still a further embodiment, the inactivated virus may be an inactivated whole virus, the genome of which provided the viral sequences of the recombinant transgene-carrying virus, or a replication defective virus comprising at least a portion of the genome from which the recombinant transgene-carrying virus was made. The replication-defective virus may or may not also carry the transgene.

Another embodiment of the method of this invention permits tolerization of a patient to the open reading frame of the therapeutic transgene. According to this method, the inactivated virus is a different virus or strain than the live virus vector, but carries and expresses the same transgene as does the live virus vector.

The inactivated virus may be prepared by conventional means. Preferably for heat inactivation, live virus is subjected to temperatures of at least about 56° C. for about 30 minutes. Similarly, the UV irradiation necessary to inactivate a virus can range from exposures of between about 100 to about 4000 rads for an exposure time of about several seconds to several hours. Other means of inactivation, such as chemical inactivation with organic solvents, toxic bleaches, imines, formalin and the like can be employed and are well-known to the art. Combinations of these conventional mechanisms of viral inactivation may also be employed to produce an inactivated virus of this invention.

In the practice of this invention, it is preferred that a high dose of the inactivated virus be administered via the oral route, as demonstrated in the following examples and figures referred to herein. However, another suitable route of administration of inactivated virus is intravenous (iv). A dose of the inactivated virus suitably high to induce tolerance is greater than about $10^{11}$ viral particles/kg patient body weight for either route of administration. More preferably, where the route is oral, a preferred amount of the inactivated virus is greater than $10^{13}$ particles/kg, and may be about, or greater than, $10^{16}$ particles/kg. Where the route is i.v., a preferred amount of the inactivated virus is greater than $10^{11}$ particles/kg, and may be about, or greater than, $10^{14}$ particles/kg.

The amount of a particular inactivated virus necessary for a particular patient according to the methods of this invention may be determined on an empirical basis by one of skill in the art. Such an amount may also be impacted by the specific virus employed (i.e., the degree to which it expresses viral antigens), and can be determined readily without resort to undue experimentation.

The inactivated virus is generally administered between about 6 hours to about 28 days before administration of the first live recombinant virus carrying the transgene to permit the immune suppression or T cell de-activation to occur before administration of the live recombinant virus. Pre-administration of inactivated virus creates a climate of immune tolerance, or at least reduced immunologic rejection, of the live recombinant virus.

Although it is not anticipated to be necessary, administration of the inactivated virus may be repeated prior to a second or subsequent administration of the live virus, in conditions such as cystic fibrosis, in which repeated transgene administration is likely to be necessary for the treatment to be effective. However, it is anticipated that only a single administration of the inactivated virus prior to the first administration of the live recombinant virus carrying the transgene will be necessary to induce long-lasting tolerance.

Immune tolerance can be mediated by several different mechanisms which include deletion, anergy and deviation of specific lymphocytes. Several mechanisms of immune tolerance are anticipated to be involved in this gene therapy method. While not wishing to be bound by theory, the mechanism by which the present invention operates may be similar to "clonal anergy", i.e., T cell non-responsiveness, causing deactivation of immune attack T cells specific to a particular antigen, resulting in a reduction in the immune response to this antigen. See, e.g., the description in International Patent Application No. WO95/27500, published Oct. 19, 1995 and incorporated herein by reference.

It is anticipated that oral tolerance to the recombinant virus may be enhanced by manipulation of antigen dosage as described above. Other factors may also enhance oral tolerance, such as the strength of costimulation and cytokine milieu. For example, oral tolerance may be enhanced by administering the inactivated virus with a selected immune modulator. An optional step in the method of this invention involves the co-administration to the patient, either concurrently with, or before or after administration of the inactivated virus, of a suitable amount of a short acting immune modulator. The selected immune modulator is defined herein as an agent capable of inhibiting the formation of neutralizing antibodies directed against the recombinant virus of this invention or capable of inhibiting cytolytic T lymphocyte (CTL) elimination of the virus. The immune modulator may interfere with the interactions between the T helper subsets ($T_{H1}$ or $T_{H2}$) and B cells to inhibit neutralizing antibody formation. Alternatively, the immune modulator may inhibit the interaction between $T_{H1}$ cells and CTLs to reduce the occurrence of CTL elimination of the recombinant virus.

A variety of useful immune modulators and dosages for use of same are disclosed, for example, in Yang et al., *J. Virol.*, 70(9) (September, 1996); International Patent Application No. WO96/12406, published May 2, 1996; and International Patent Application No.PCT/US96/03035, all incorporated herein by reference.

The following examples and analyses of the method of this invention employ a cystic fibrosis (CF) gene therapy model, using a recombinant replication-defective human adenovirus type 5 (rAd5) as a vector and *Escherichia coli* lacZ as transgene. However, it should be clear to one of skill in the art that the methods of this invention have broad application to other disorders, other recombinant viruses and inactivated viruses and other transgenes. The scope of this invention is thus not limited to the components of the following examples used to illustrate the invention.

EXAMPLE 1

Antigen Selection Based on Ability to Induce Oral Tolerance

Since the form of an antigen is known to play a pivotal role in the development of oral immunity versus tolerance, three types of viral antigens were examined for their ability to induce oral tolerance or immunity. These include a live recombinant adenovirus, serotype 5 (Ad5) carrying a gene encoding beta-galactosidase (LacZ). This recombinant virus is described in Y. Yang et al, *J. Virol.*, 69(4):2004–2015 (1995) as H5.010CMVLacZ. It is based on an Ad5 sub360 backbone deleted of E1a and E1b (1.0 to 9.6 map units) as well as 400 bp of the E3 region. LacZ is expressed from a cytomegalovirus promoter. For ease of reference, this recombinant virus is referred to herein as "live rAd5-LacZ".

A second viral antigen is heat-inactivated, ultraviolet (UV)-irradiated rAd5-LacZ. The recombinant virus was heated for 0.5 hour at 56° C., followed by exposure to ultraviolet radiation of about 1000 rads for several minutes. The third antigen is live rAd5-LacZ-infected syngeneic splenocytes.

To determine whether these antigen preparations induce oral tolerance, C57BL/6 mice were first fed with $10^{12}$ virus particles of one of the above-described live or inactivated virus vectors, or with $10^7$ splenocytes infected with $10^{12}$ live virus particles.

Two days later, the mice were challenged with $5 \times 10^{10}$ particles of live rAd5-LacZ intratracheally. Mice were sacrificed 10 days after the challenge and their spleens harvested. The splenocytes were tested for anti-adenoviral immune responses in a conventional proliferation assay as described in Yang et al., *J. Virol.*, 69:2004 (1995), incorporated herein by reference.

Surprisingly, oral administration of heat-inactivated, UV-irradiated rAd5-LacZ induced profound immune suppression (tolerance) of anti-adenovirus immunity. In contrast, oral administration of live rAd5-LacZ or live rAd5-LacZ-infected syngeneic splenocytes induced no tolerance.

EXAMPLE 2

Tolerization of Adenovirus-Specific Helper T Cells

A. Tolerance/Challenge Experiment

Three groups of C57BL/6 mice were fed either with phosphate buffered saline (PBS) or $10^{12}$ particles of heat-inactivated, UV-irradiated rAd5-LacZ ("dead" virus). As a control, the third group of mice was injected intravenously with $10^{12}$ particles of dead rAd5-LacZ to determine whether tolerance could be induced via an intravenous route of administration. Two days later, mice were challenged with $5 \times 10^{10}$ particles of live rAd5-LacZ intratracheally. Mice were sacrificed 10 days after the challenge and their spleens harvested.

The splenocytes were tested for anti-adenovirus immune responses in a proliferation assay and a cytokine assay described below. The experiment was repeated twice with similar results.

B. Proliferation Assay

A proliferation assay was conducted as described in Yang et al., *J. Virol.*, 69:2004 (1995), incorporated by reference. Briefly described, splenocytes, $1 \times 10^6$ cells/well, were cultured in 0.2 ml serum-free medium containing various concentrations of dead rAd5-LacZ. 1 $\mu$Ci of $^3$H-thymidine was added to each culture 72 hours after initiation of the culture and cells were harvested and radioactivity measured 16 hours later.

The results of the proliferation assay can be seen in FIG. 1A. Radioactivity is measured in counts per minute of the tritiated thymidine incorporated into the DNA. These data points are proportional to cell proliferation. Each data point represents a mean from a minimum of 3 mice. The standard deviations of CPM data are within 25% of the means.

As illustrated in FIG. 1A, both oral and intravenous administrations of dead rAd5-LacZ suppressed splenocyte proliferation when compared with PBS controls. Splenocytes decreased in number for the mice administered the inactivated virus, both orally and intravenously in comparison to the control.

C. Cytokine Assays

To assess the mechanisms behind the immune suppression and cell proliferation, cytokine assays were conducted as described in Chen et al., *Science*, 265:1237 (1994), incorporated by reference.

Briefly described, culture supernatants were collected at 40 hours and cytokine concentration was determined by ELISA. Each data point represents a mean from a minimum of 3 mice and the standard deviations of the cytokine data are within 20% of the means. The results of the cytokine assays can be seen for IL-2 in FIG. 1B, for IFN-γ in FIG. 1C, and for IL-10 in FIG. 1D.

Oral, but not intravenous, pre-administration of inactivated rAd5-LacZ suppressed IL-2 production. However, both IFN-γ (FIG. 1C) and IL-10 (FIG. 1D) were suppressed in response to administration of orally or i.v. administered inactivated virus in comparison to the control.

EXAMPLE 3

Tolerization of Virus-Specific Cytotoxic T Cells

To test whether oral or intravenous administration of dead viral antigens affects cytotoxic T cell responses, anti-adenovirus-induced cytotoxicity was tested by $^3$H-thymidine release assay (JAM assay) as described in P. Metzinger, *J. Immunol. Meth.*, 145:185 (1991), incorporated herein by reference.

Briefly described, mice were treated as in Example 2 above. Their splenocytes were cultured in vitro for four days with rAd5-LacZ and their specific cytotoxicity tested using a syngeneic fibroblast cell line infected with rAd5-LacZ. CTLs will lyse cells with the viral antigens displayed on their surfaces. The cells are loaded with radio-label and the release of label is proportional to cell lysis.

The results are shown in FIG. 2. Each data point represents a mean from a minimum of 3 mice. The standard deviations are with 15% of the means. The experiment was repeated twice with similar results.

Both oral and intravenous administrations of dead rAd5-LacZ suppressed the generation of adenovirus-specific cytotoxic T cells, although under these conditions, the oral route appeared to be more effective than the intravenous route.

EXAMPLE 4

Effect on Humoral Immunity

To test whether oral administration of inactivated rAd5-LacZ suppresses humoral immunity, anti-adenovirus antibody responses in mice fed inactivated rAd5-LacZ were examined by conventional methods as described in Yang et al., *J. Virol.*, 69:2004 (1995), incorporated by reference herein. Briefly described, mice were treated as described in Example 2 and the adenovirus-specific antibody isotype was determined in bronchial alveolar lavage (BAL) by using enzyme-linked immunosorbent assay (ELISA).

The resulting data showed that although mucosal IgA was not drastically suppressed by oral administration of inactivated rAd5-LacZ, a 40–60% suppression was observed for anti-adenovirus IgM and IgG responses. These data strongly suggest that specific immunologic tolerance can be induced by oral or intravenous administration of inactivated virus and that oral route may be more effective than intravenous route.

EXAMPLE 5

X-gal Histochemistry

LacZ gene expression was examined by X-gal histochemistry according to standard procedures [see, e.g., procedures described in J. Price et al, *Proc. Natl. Acad. Sci., USA,* 84:156–160 (1987)]. Mice were treated as described in Example 2 and their lung tissue examined at various times after live virus challenge.

As indicated in the FIGS. 3A through 3F, LacZ gene expression lasted approximately 17 days in lung tissue of non-tolerized (PBS fed) mice. The expression of the transgene was prolonged to at least 28 days in mice fed $10^{12}$ dead rAd5-LacZ, according to this invention.

All references recited above are incorporated herein by reference. Numerous modifications and variations of the present invention are included in the above-identified specification and are expected to be obvious to one of skill in the art. Such modifications and alterations to the compositions and processes of the present invention, such as selections of different transgenes or selection or dosage of the vectors or immune modulators are believed to be within the scope of the claims appended hereto.

What is claimed is:

1. A method for reducing an anti-adenovirus immune response in a mammalian subject to the administration of a live recombinant adenovirus carrying a transgene of interest, said method comprising:

(a) administering to said mammal, via a route of administration which is either oral or intravenous, an inactivated adenovirus which has capsid proteins or expresses viral proteins that arc antigenically related to the capsid and viral proteins of said live recombinant adenovirus, said inactivated adenovirus being administered in an amount sufficient to reduce the anti-adenovirus immune response to said live recombinant adenovirus, and (b) administering to said mammal said live recombinant adenovirus, wherein said administering step (a) suppresses the immune response directed against said live recombinant adenovirus upon administering step (b).

2. The method according to claim 1 wherein said inactivated adenovirus is administered orally.

3. The method according to claim 1 wherein said inactivated adenovirus is administered intravenously.

4. The method according to claim 1 wherein said amount of said inactivated adenovirus is greater than about $10^{11}$ adenovirus particles/kg patient body weight.

5. The method according to claim 1 wherein said inactivated adenovirus is a whole adenovirus.

6. The method according to claim 1 wherein said inactivated adenovirus is a replication-defective adenovirus.

7. The method according to claim 1 wherein said inactivated adenovirus comprises the recombinant adenovirus carrying the transgene of interest, wherein said recombinant retrovirus has been previously inactivated.

8. The method according to claim 1, wherein said inactivated adenovirus has an identical viral sequence to the recombinant adenovirus carrying the transgene of interest, but said inactivated adenovirus does not carry said transgene of interest.

9. The method according to claim 1, wherein said inactivated adenovirus is administered between about 6 hours to about 28 days before administration of said live recombinant adenovirus.

10. The method according to claim 1 wherein said inactivated adenovirus is re-administered before a second and subsequent administration of said live recombinant adenovirus.

11. The method according to claim 1, wherein said inactivated adenovirus is prepared by a method selected from the group consisting of thermal inactivation, physical inactivation, chemical inactivation and combinations thereof.

* * * * *

UNITED STATES PATENT AND TRADEMARK OFFICE
CERTIFICATE OF CORRECTION

PATENT NO. : 6,211,160 B1
DATED : April 3, 2001
INVENTOR(S) : J. Wilson et al.

It is certified that error appears in the above-identified patent and that said Letters Patent is hereby corrected as shown below:

Column 10,
Line 38, replace "retrovirus" with -- adenovirus --.

Signed and Sealed this

Thirteenth Day of August, 2002

*Attest:*

*Attesting Officer*

JAMES E. ROGAN
*Director of the United States Patent and Trademark Office*